United States Patent
Biolchini, Jr.

(10) Patent No.: US 7,758,609 B1
(45) Date of Patent: Jul. 20, 2010

(54) AMBIDEXTROUS LOCKING CLAMP

(76) Inventor: Robert F. Biolchini, Jr., 692 E. Hansen, Jackson, WY (US) 83001

(*) Notice: Subject to any disclaimer, the term of this patent is extended or adjusted under 35 U.S.C. 154(b) by 1114 days.

(21) Appl. No.: 10/909,623

(22) Filed: Aug. 2, 2004

(51) Int. Cl.
*A61B 17/28* (2006.01)
*A61B 17/29* (2006.01)
*B25B 7/00* (2006.01)

(52) U.S. Cl. .................. 606/208; 606/205; 81/300; 81/302; 81/315

(58) Field of Classification Search ............ 606/208, 606/206, 205, 210, 108; 81/300, 302, 315, 81/318–320, 324–328; 30/232, 254, 256, 30/262, 341, 194, 251; 16/110.1–114, 405–430; 294/82.1–120; 292/256–278
See application file for complete search history.

(56) References Cited

U.S. PATENT DOCUMENTS

| | | | |
|---|---|---|---|
| 3,417,752 A * | 12/1968 | Butler ................ | 606/147 |
| 3,913,586 A | 10/1975 | Baumgarten | |
| 3,978,584 A | 9/1976 | Mayer | |
| 4,452,246 A * | 6/1984 | Bader et al. ........... | 606/147 |
| 4,823,792 A * | 4/1989 | Dulebohn et al. ...... | 606/151 |
| 5,133,737 A * | 7/1992 | Grismer ................ | 606/205 |
| 5,176,702 A | 1/1993 | Bales | |
| 5,626,608 A | 5/1997 | Cuny | |
| 5,738,659 A * | 4/1998 | Neer et al. ............ | 604/154 |
| 6,223,440 B1 | 5/2001 | Rashman | |
| 6,397,478 B1 | 6/2002 | Bornancini | |
| 2004/0106947 A1 | 6/2004 | Propp | |

* cited by examiner

*Primary Examiner*—Anhtuan T Nguyen
*Assistant Examiner*—Amy T Lang
(74) *Attorney, Agent, or Firm*—David A. Guerra

(57) ABSTRACT

An ambidextrous locking clamp system for providing a user the ability to alter the configuration of a hand operated device allowing a right or left handed user to operate the device. The device has a hingedly connected first and second elongated member each with a finger engaging member and a working head. At least two inter-engaging latching members are removably attached to the first and the second elongated members. The latching members are symmetrical, interchangeable, and reversible, allowing a user to change the configuration of the ambidextrous device. The latching members can be retained to the elongated members by a rotatably lever, a removable retaining cap, or a removable retaining pin. Additionally, the latching members can be incorporated into removable finger engaging members, thereby allowing the entire finger engaging member and latching member to be removed, interchanged or reversed.

15 Claims, 18 Drawing Sheets

AMBIDEXTROUS LOCKING CLAMP

BACKGROUND OF THE INVENTION

1. Field of the Invention

The present invention relates to an ambidextrous locking clamp system for use in connection with clamping instruments, such as surgical clamps, forceps, or hemostats. The ambidextrous locking clamp system has particular utility in connection with manipulating objects with a tool having removable and interchangeable locking assemblies.

2. Description of the Prior Art

Ambidextrous locking clamps, forceps or hemostats are desirable for allowing a right or left-handed user to use a single hand operated clamp, forceps or hemostat device. These hand operated devices have been manufactured in the past for either a right hand or left hand user. This manufacturing process has some disadvantages in that the manufacturer would have to make a decision to how many right handed and left handed devices to fabricate. In most cases the decision is made to manufacture more right-handed devices than left handed devices. Therefore, it is well known that it is very difficult for a left-handed user to operate a right-handed device.

Hand operated locking clamps, forceps and hemostats are well known. These devices include a pair of elongated members joined by a hinge. The hinge is usually a hinge pin extending through both elongated members. One end of the elongated members features a working head, usually a griping jaw or cutting edges. The other end of the elongated members features a finger engaging loop, with a set of ratchet teeth extending out therefrom towards the ratchet teeth of the finger loop of the second elongated member. The ratchet teeth are orientated so that they engage each other when the finger loop ends are brought together. These devices are mainly used in the medical industry for a wide variety of uses, but they are also used in the fly fishing, model building, and electrical industries.

During operation of a standard right handed hand operated device, the user inserts his or her thumb into one loop, the middle finger in the opposite loop, and the index finger would rest on the top of the middle finger loop for support and control of the device. To engage the working head the user squeezes the thumb and middle finger together guided by the index finger. The device is locked in the close position by further squeezing the loops together until the ratchet teeth members engage each other. To release, the thumb pushes away from the palm of the hand and the middle finger pulls toward the palm of the hand. This motion makes the ratchet teeth members flex away from each other and disengage.

The difficulty lies when a left-handed user tries to operate a right-handed device. It is difficult for a left-handed user to pull with the thumb and push with the middle finger. This is not a natural hand motion.

The use of locking clamps is known in the prior art. For example, U.S. Pat. No. 6,397,478 to Jose Carlos Mario Bornancini; U.S. Pat. No. 3,978,584 to John Mayer; U.S. Pat. No. 3,913,586 to Baumgarten; U.S. Pat. No. 6,223,440 to Rashman; United States Patent Application Publication 2004/0106947 to Propp et al.; U.S. Pat. No. 5,626,608 Cuny et al.; and U.S. Pat. No. 5,176,702 to Bales et al.

While the above-described devices fulfill their respective, particular objectives and requirements, the aforementioned patents do not describe an ambidextrous hand operated device that allows the use of the device by a right or left handed user through the interchanging of components.

Therefore, a need exists for a new and improved ambidextrous locking clamp system that can be used for manipulating objects with a tool having removable and interchangeable components. In this regard, the present invention substantially fulfills this need. In this respect, the ambidextrous locking clamp system according to the present invention substantially departs from the conventional concepts and designs of the prior art, and in doing so provides an apparatus primarily developed for the purpose of manipulating objects with a tool having removable and interchangeable locking assemblies.

SUMMARY OF THE INVENTION

In view of the foregoing disadvantages inherent in the known types of hand operated locking devices now present in the prior art, the present invention provides an improved ambidextrous locking clamp system, and overcomes the above-mentioned disadvantages and drawbacks of the prior art. As such, the general purpose of the present invention, which will be described subsequently in greater detail, is to provide a new and improved ambidextrous locking clamp system and method which has all the advantages of the prior art mentioned heretofore and many novel features that result in a ambidextrous locking clamp system which is not anticipated, rendered obvious, suggested, or even implied by the prior art, either alone or in any combination thereof.

To attain this, the present invention essentially comprises an ambidextrous locking clamp system for providing a user the ability to alter the configuration of a hand operated device allowing a right hand or left hand user to operate the device, wherein the ambidextrous locking clamp system has having a first elongated member including a finger engaging member and a working head, a second elongated member including a finger engaging member and a working head, wherein the second elongated member is hingedly connected to the first elongated member, and at least two latching members that are removably attached to the first and second elongated members.

Additionally, the present invention may comprise an ambidextrous locking clamp system having a first elongated member including a finger engaging member receiving assembly and a working head opposite of the finger engaging member receiving assembly, a second elongated member including a finger engaging member receiving assembly and a working head opposite of the finger engaging member receiving assembly, at least two finger engaging members removably attached to the finger engaging member receiving assemblies of the first and second elongated members, and at least two retaining caps for retaining the finger engaging members to the finger engaging member receiving assemblies. The second elongated member is hingedly connected to the first elongated member There has thus been outlined, rather broadly, the more important features of the invention in order that the detailed description thereof that follows may be better understood and in order that the present contribution to the art may be better appreciated.

The invention may also include a variety of means to retain the latching members to the first and second elongated members, such as, but not limited to, rotating levers, removable retaining caps, and removable retaining pins. There are, of course, additional features of the invention that will be described hereinafter and which will form the subject matter of the claims attached.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved ambidextrous locking clamp system that has all of the advantages of the prior art locking clamps and none of the disadvantages.

It is another object of the present invention to provide a new and improved ambidextrous locking clamp system that may be easily and efficiently manufactured and marketed.

An even further object of the present invention is to provide a new and improved ambidextrous locking clamp system that has a low cost of manufacture with regard to both materials and labor, and which accordingly is then susceptible of low prices of sale to the consuming public, thereby making such ambidextrous locking clamp system economically available to the buying public.

Still another object of the present invention is to provide a new ambidextrous locking clamp system that provides in the apparatuses and methods of the prior art some of the advantages thereof, while simultaneously overcoming some of the disadvantages normally associated therewith.

Lastly another object of the present invention is to provide an ambidextrous locking clamp system for manipulating objects with a tool having removable and interchangeable locking assemblies. This allows the use of the hand operated device by either a right or left handed user.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various figures.

DESCRIPTION OF THE PREFERRED EMBODIMENT

Figure 1:
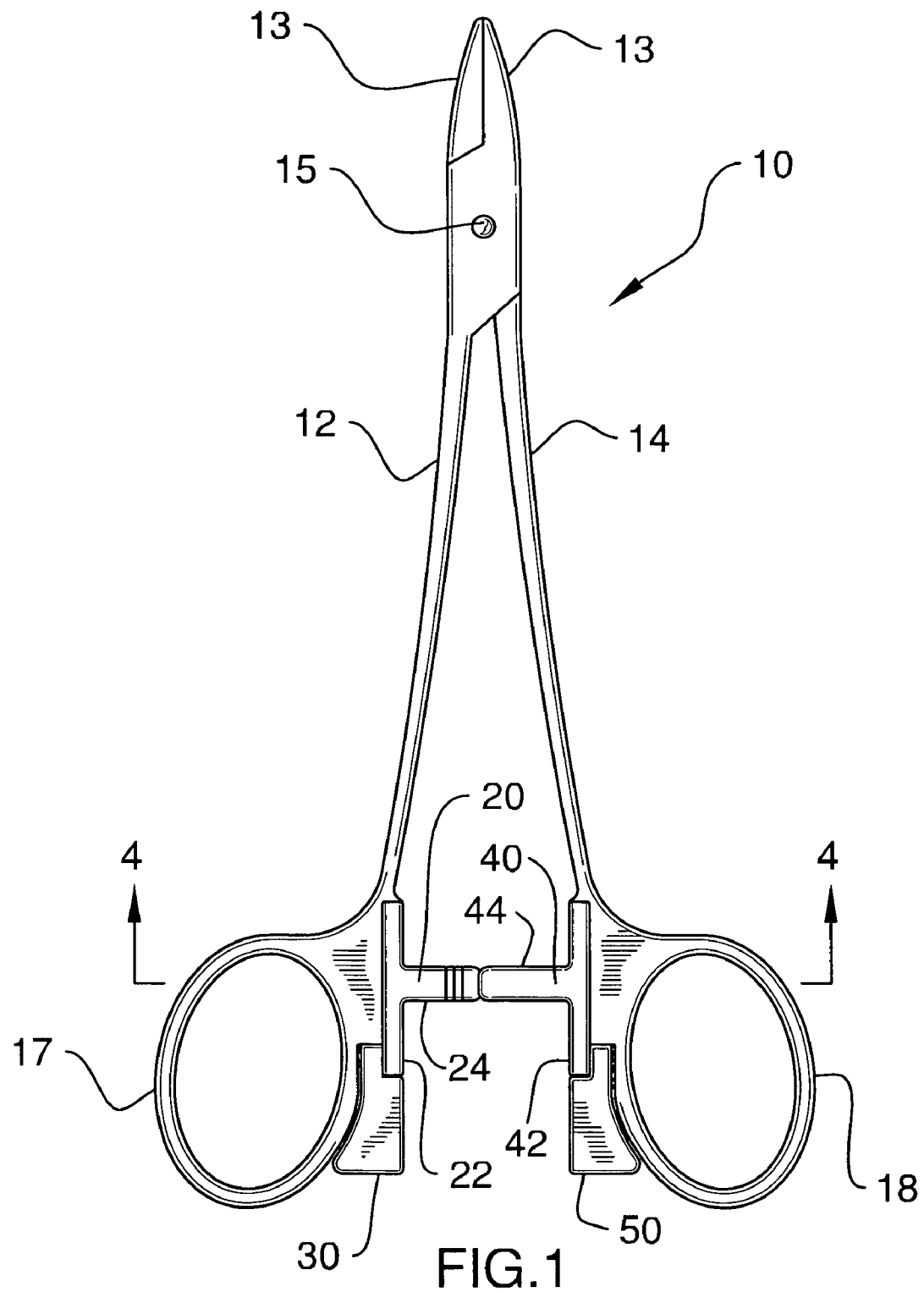
FIG. 1 is a front elevational view of the ambidextrous locking clamp system constructed in accordance with the principles of the present invention.

Referring now to the drawings, and particularly to FIGS. 1-23, a first embodiment of the ambidextrous locking clamp system of the present invention is shown and generally designated by the reference numeral 10.

In FIG. 1, a new and improved ambidextrous locking clamp system 10 of the present invention for allowing the use of a hand operated device by a right or left handed user is illustrated and will be described. More particularly, the ambidextrous locking clamp system 10 has a first elongated member 12 and a second elongated member 14 each having a working head 13, wherein the working heads can be, but not limited to, a gripping jaw or a cutting edge. The second elongated member 14 is connected to the first elongated member 12 via a hinge 15. The first and second elongated members 12 and 14 each have a finger engaging member 17 and 18 located opposite of the working heads 13. A first lever 30 and second lever 50 are pivotally attached to the finger engaging members 17 and 18, and are orientated so that the levers are facing each other. Additionally, a first latching member 20 is removably attached to the finger engaging member 17 and a second latching member 40 is removably attached to the finger engaging member 18. The first and second elongated members 12 and 14 can be made from any suitable material having reflex memory.

Figure 2:
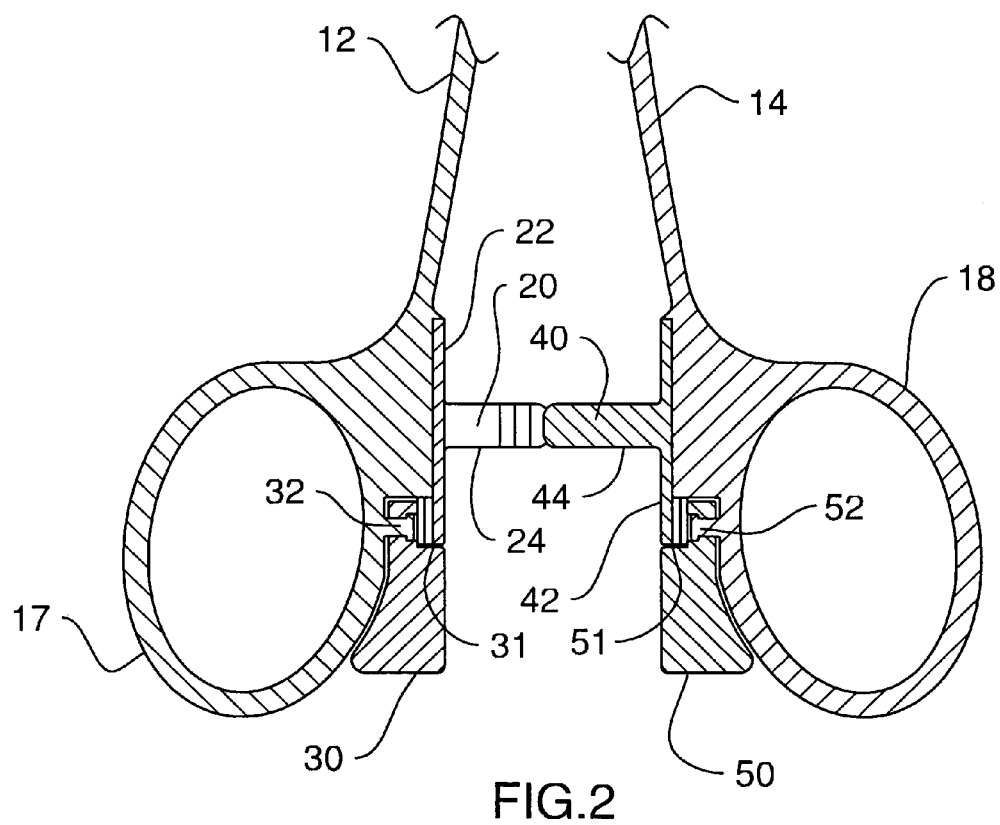
FIG. 2 is an enlarged cross-sectional view of the ambidextrous locking clamp system of the present invention.
Figure 3:
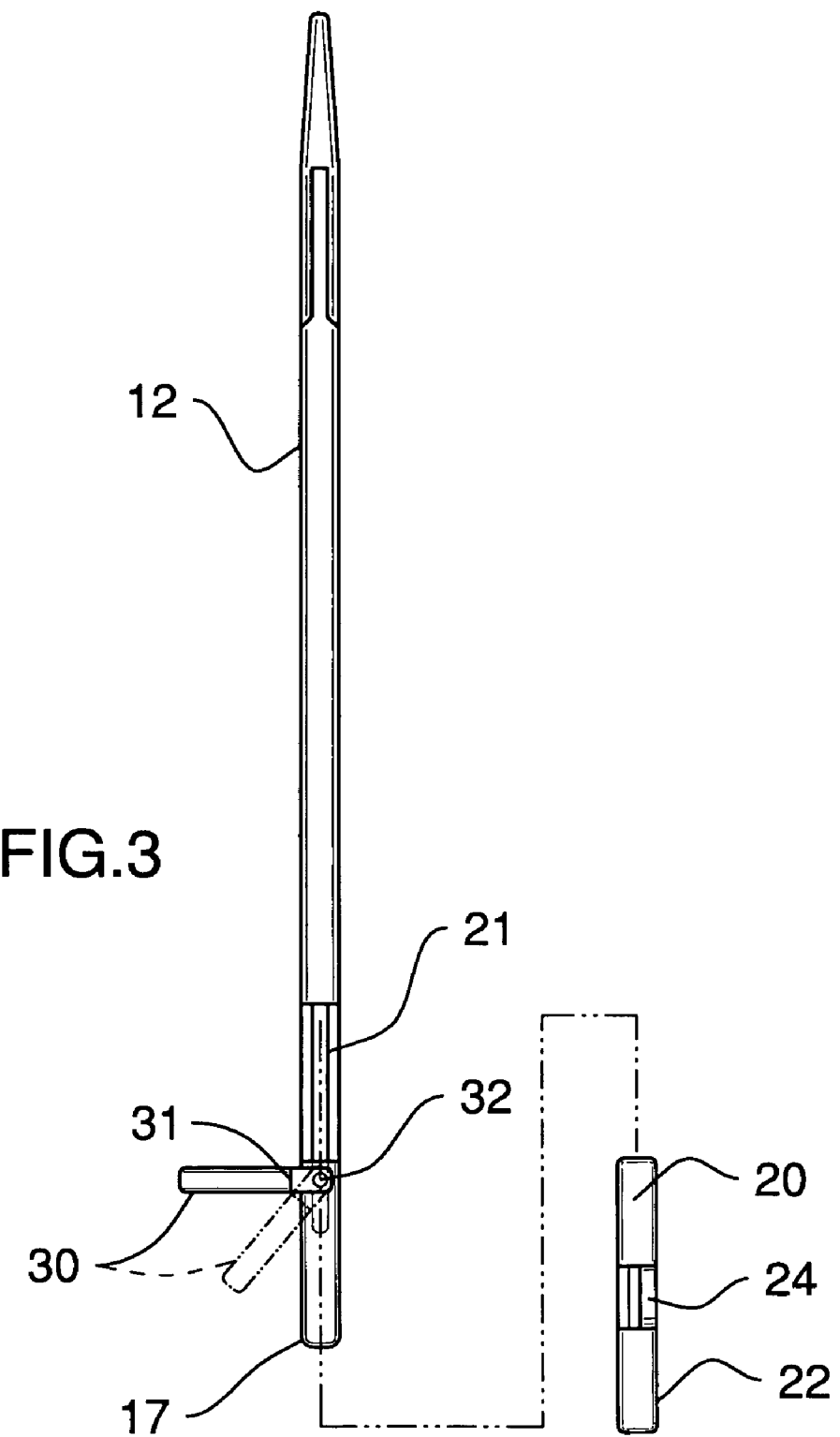
FIG. 3 is an exploded side plane view of the ambidextrous locking clamp system of the present invention.

The levers 30 and 50 have an extended portion for easy operation by the fingers of a user, and are contoured to conform to the shape of the finger engaging members 17 and 18. A pivot pin 32 and 52 extend from the finger engaging members 17 and 18, and through levers 30 and 50, allowing the levers to rotate. The levers 30 and 50 have an extension 31 and 51 for retaining the first and second latching members 20 and 40 on the finger engaging members 17 and 18 when the levers are aligned with the longitudinal axis of the first and second elongated members 12 and 14. When the levers 30 and 50 are rotated to a position perpendicular to the first and second elongated members 12 and 14, the extensions 31 and 51 are able to be moved out of engagement with the first and second latching members 20 and 40, thereby allowing the first and second locking members to slide past the extensions 31 and be removed from finger engaging members 17 and 18. This is best illustrated in FIGS. 2 and 3.

The first and second latching members 20 and 40 each have an elongated base 22 and 42 and a latch arm 24 and 44 extending out from each elongated base. The latch arms 24 and 44 feature a plurality of teeth 26 and 46, which are adapted to join and lock together when engaged. The teeth 26 and 46 are able to disengage when pulled apart by the flexing of the first and second elongated members 12 and 14 when an opposing force is applied to the finger engaging members 17 and 18.

Figure 4:
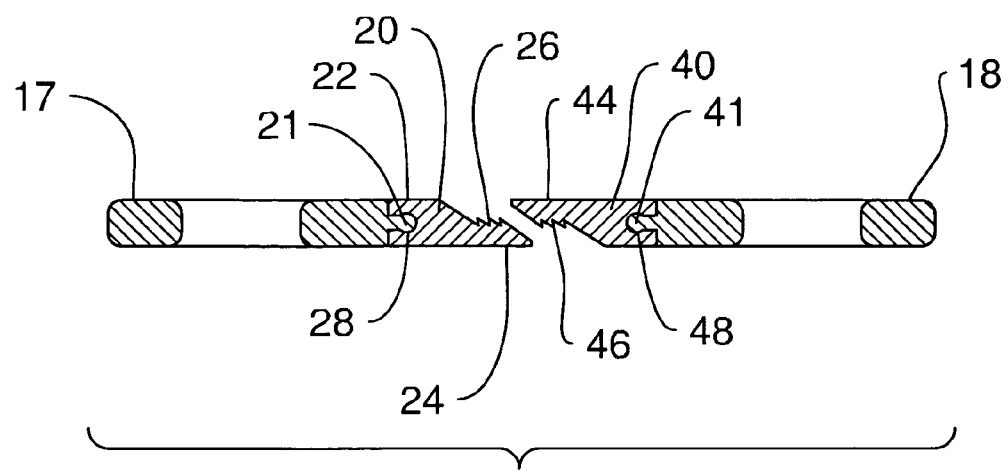
FIG. 4 is a cross-sectional view the locking assembly of the ambidextrous locking clamp system of the present invention.
Figure 5:
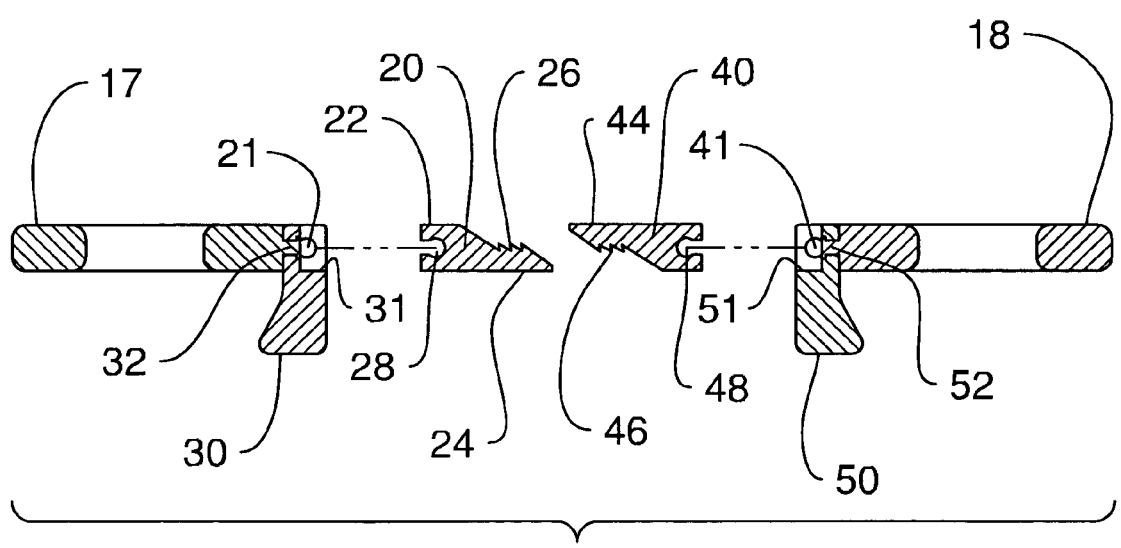
FIG. 5 is an exploded cross-sectional view of the locking assembly of the ambidextrous locking clamp system of the present invention.

The elongated base 22 and 42 of the first and second latching members 20 and 40 each have a channel 28 and 48 running the length of the elongated base. The channels 28 and 48 are adapted to slide on and be retained by a protrusion 21 and 41 extending out from the finger engaging members 17 and 18 and adjacent to the levers 30 and 50. The configuration of the channels 28 and 48 and the protrusions 21 and 41 allow the first and second latching members 20 and 40 to slide over the protrusion, but at the same time not allowing the latching members to be pulled off the protrusions in a direction perpendicular to the sliding motion. FIGS. 4 and 5 best illustrate one possible example of the channel and protrusion configuration.

The first and second latching members 20 and 40 are symmetrical so that they may be removed, inverted and then replaced, thereby changing the orientation of the latching members and allowing a right or left handed user to operate the device 10. Furthermore, other configurations of the first and second latching members 20 and 40 maybe used in place of the above described latching members.

Figure 6:
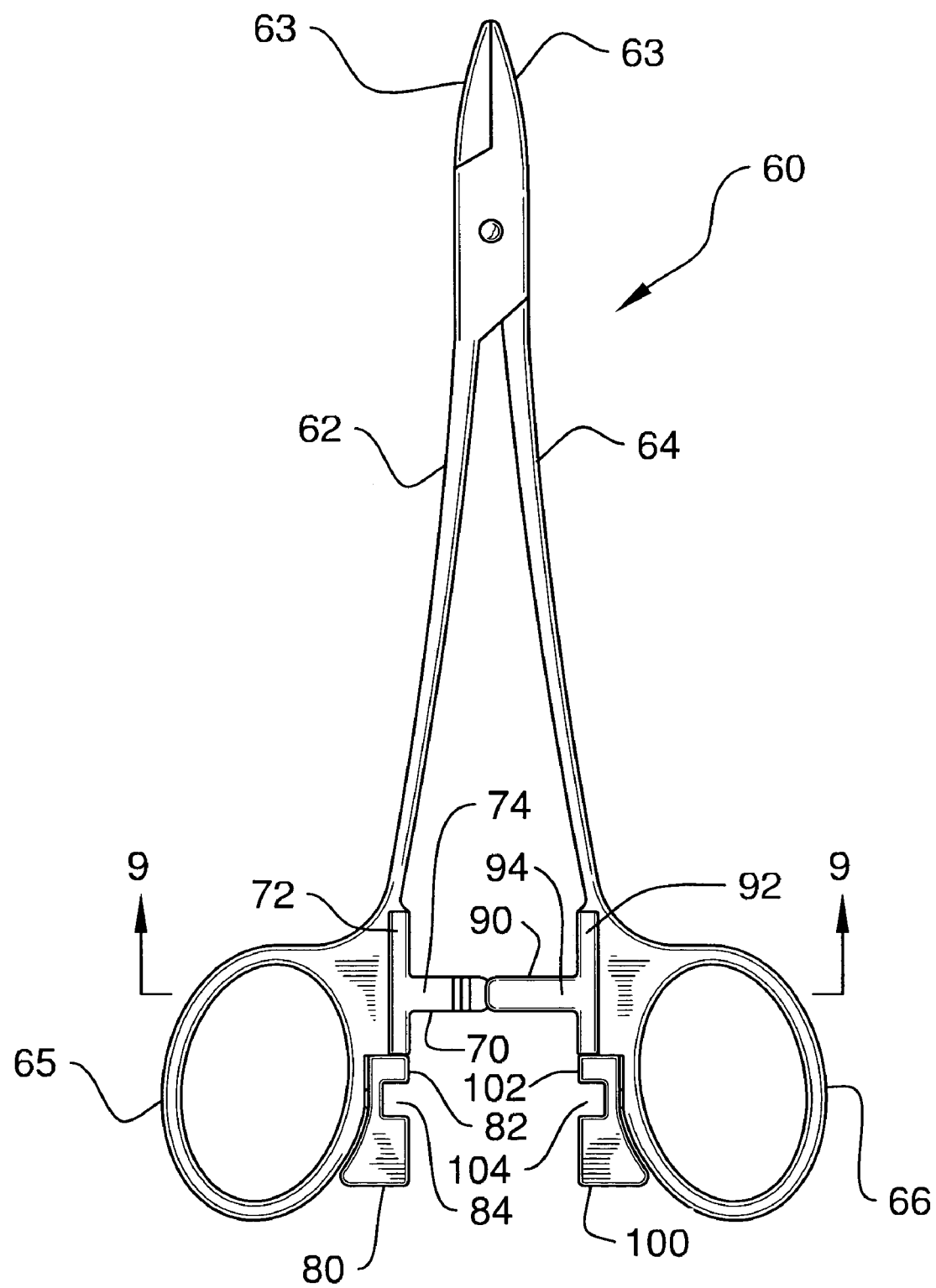
FIG. 6 is a front elevational view of a second alternate embodiment of the ambidextrous locking clamp system of the present invention.

Referring now to FIG. 6, a second alternate embodiment of the ambidextrous locking clamp system of the present invention is shown and generally designated by the reference numeral 60. More particularly, the ambidextrous locking clamp system 60 has a first elongated member 62 and a second elongated member 64 each having a working head 63, wherein the working heads can be, but not limited to, a gripping jaw or a cutting edge. The second elongated member 64 is connected to the first elongate member 62 via a hinge. The first and second elongated members 62 and 64 have a finger engaging member 65 and 66 located opposite of the working heads 63. A first lever 80 and second lever 100 are pivotally attached to the finger engaging members 65 and 66, and are orientated so that the levers are facing each other. Additionally, a first latching member 70 is removably attached to the finger engaging member 65 and a second latching member 90 is removably attached to the finger engaging member 66.

Figure 7:
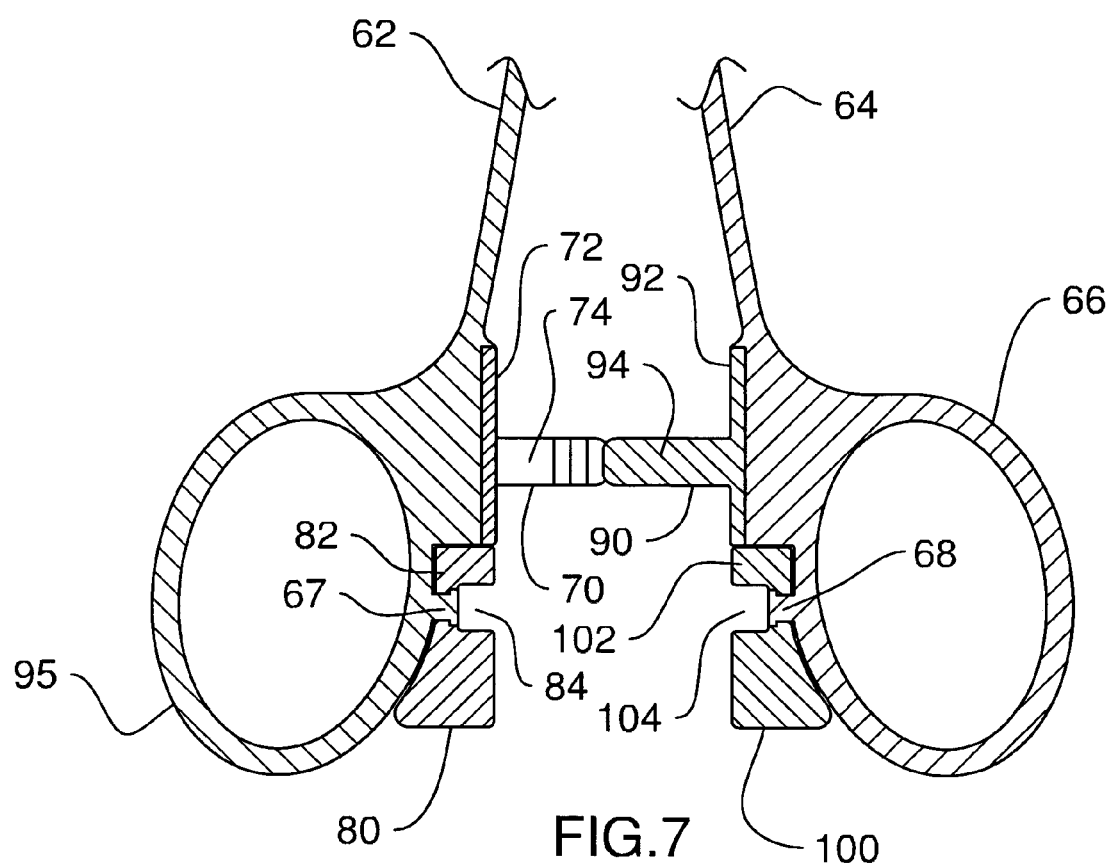
FIG. 7 is an enlarged cross-sectional view of the second alternate embodiment of the present invention.
Figure 8:
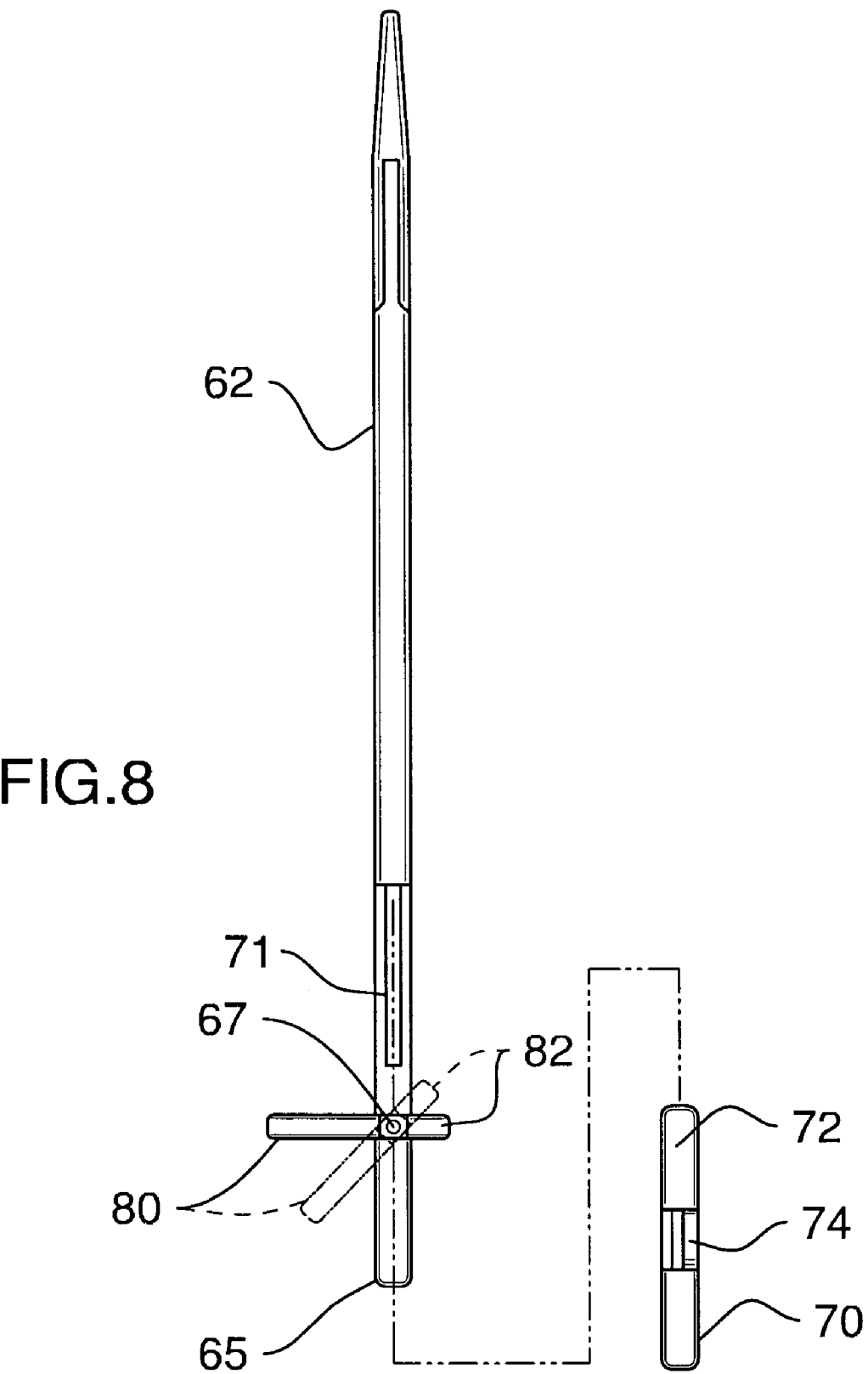
FIG. 8 is an exploded side plane view of the second alternate embodiment of the second alternate embodiment of the present invention.

The levers 80 and 100 have an extended portion for easy operation by the fingers of a user, and are contoured to conform to the shape of the finger engaging members 65 and 66. A pivot pin 67 and 68 extend from the finger engaging members 65 and 66, and through levers 80 and 100, allowing the levers to rotate. The levers 80 and 100 have an extension 82 and 102 for retaining the first and second latching members 70 and 90 on the finger engaging members 65 and 66 when the levers are aligned with the longitudinal axis of the first and second elongated members 62 and 64. A notch 84 and 104 is defined in the levers 80 and 100 for allowing the first and second latching members 70 and 90 to pass therethrough. When the levers 80 and 100 are rotated so they are perpendicular to the first and second elongated members 62 and 64, the extensions 82 and 102 are moved out of engagement with the first and second latching members 70 and 90, and the notches 84 and 104 are exposed to the first and second latching members, thereby allowing the first and second locking members to slide through the notches and removed from finger engaging members 65 and 66. This is best illustrated in FIGS. 7 and 8.

The first and second latching members 70 and 90 each have an elongated base 72 and 92 and a latch arm 74 and 94 extending out from each elongated base. The latch arms 74 and 94 feature a plurality of teeth 76 and 96, which are adapted to join and lock together when engaged. The teeth 76 and 96 are able to disengage when pulled apart by the flexing of the first and second elongated members 62 and 64 when an opposing force is applied to the finger engaging members 65 and 66.

Figure 9:
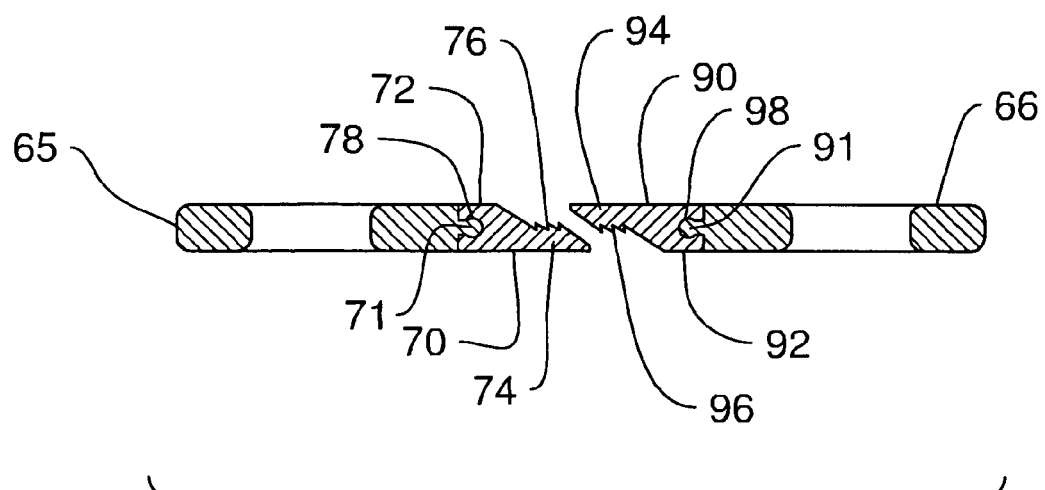
FIG. 9 is a cross-sectional view of the locking assembly of the second alternate embodiment of the present invention.
Figure 10:
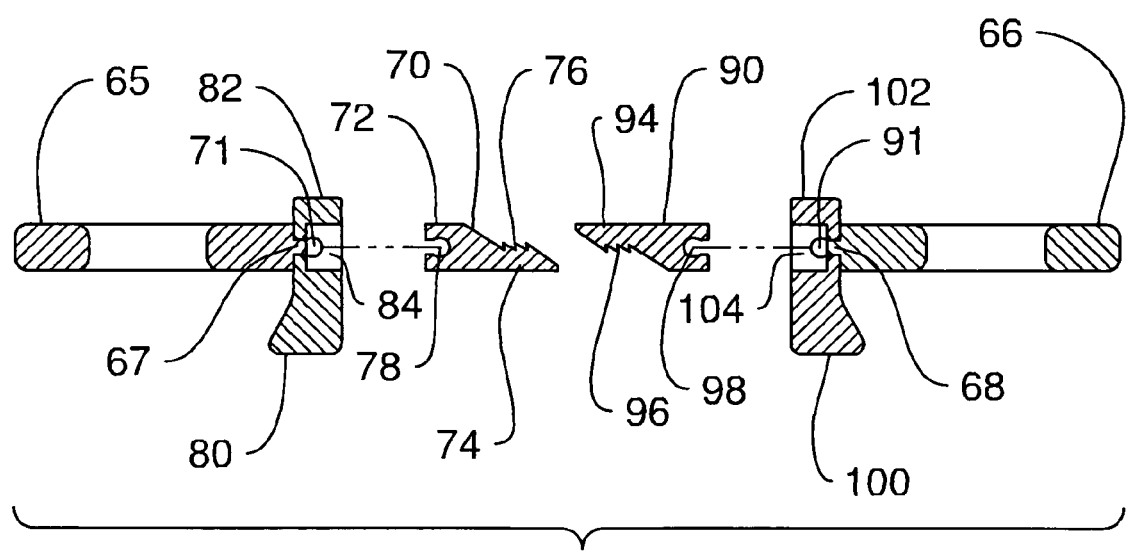
FIG. 10 is an exploded cross-sectional view of the locking assembly of the second alternate embodiment of the present invention.

The elongated base 72 and 92 of the first and second latching members 70 and 90 each have a channel 78 and 98 running the length of the elongated base. The channels 78 and 98 are adapted to slide and be retained by a protrusion 71 and 91 extending out from the finger engaging members 65 and 66 and adjacent to the levers 80 and 100. The configuration of the channels 78 and 98 and the protrusions 71 and 91 allow the first and second latching members 70 and 90 to slide over the protrusion, but at the same time not allowing the latching members to be pulled off the protrusions in a direction perpendicular to the sliding motion. FIGS. 9 and 10 best illustrate one possible example of the channel and protrusion configuration.

The first and second latching members 70 and 90 are symmetrical so that they may be removed, inverted and then replaced, thereby changing the orientation of the latching members and allowing a right or left handed user to operate the device 60. Furthermore, other configurations of the first and second latching members 70 and 90 may be used in place of the above described latching members.

Figure 11:
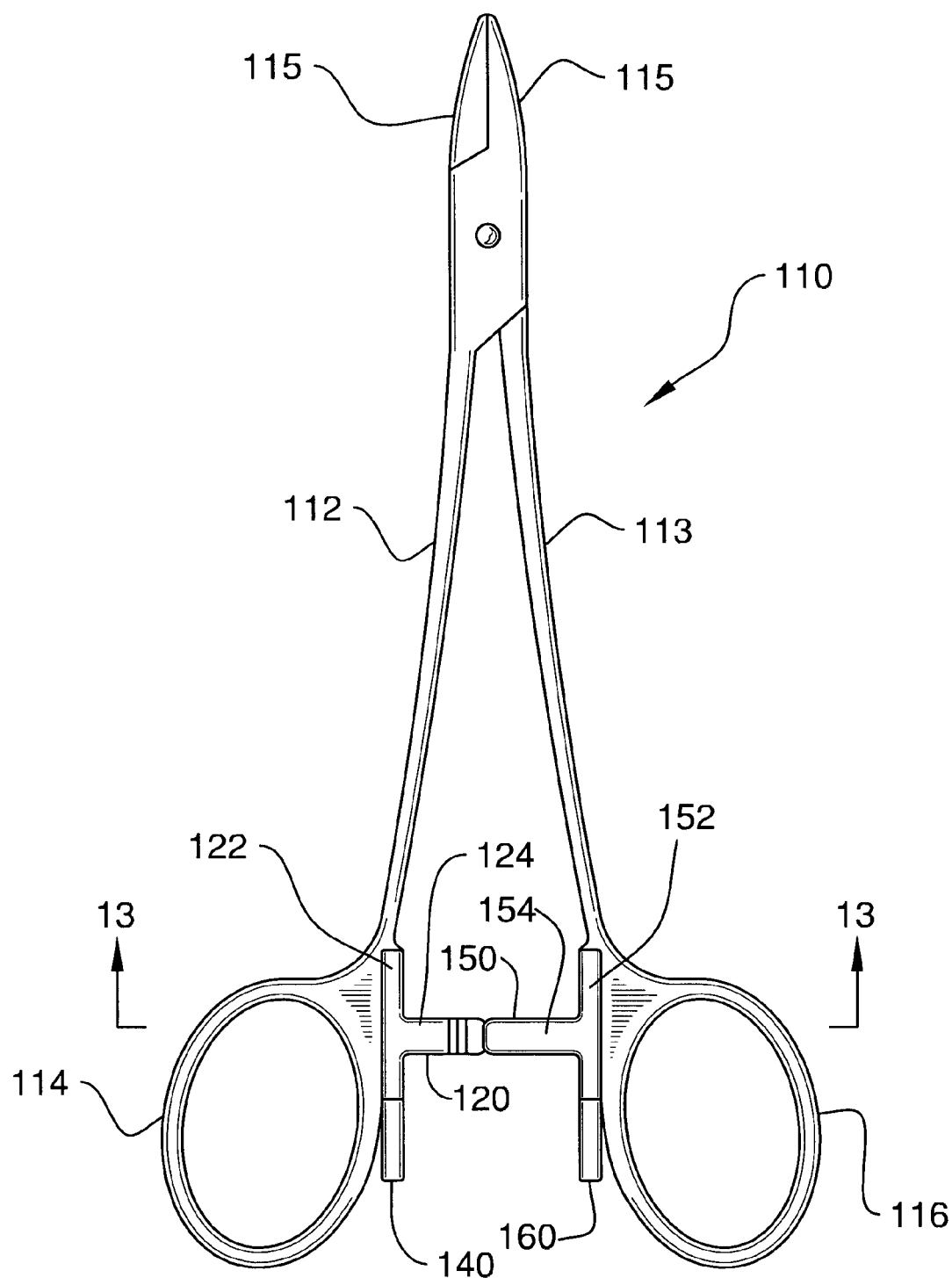
FIG. 11 is a front elevational view of a third alternate embodiment of the ambidextrous locking clamp system of the present invention.

Referring now to FIG. 11, a third alternate embodiment of the ambidextrous locking clamp system of the present invention is shown and generally designated by the reference numeral 110. More particularly, the ambidextrous locking clamp system 110 has a first elongated member 112 and a second elongated member 113 each having a working head 115, wherein the working heads can be, but not limited to, a gripping jaw or a cutting edge. The second elongated member 113 is connected to the first elongate member 112 via a hinge. The first and second elongated members 112 and 113 have a finger engaging member 114 and 116 located opposite of the working heads 115. A first retaining cap 140 and second retaining cap 160 are threadably attached to the finger engaging members 114 and 116, and are orientated so that the centerline of the caps are aligned with the longitudinal axis of the first and second elongated members 112 and 113. The retaining caps 160 can also be orientated in any alternate position to the first and second elongated members 112 and 113. Additionally, a first latching member 120 is removably attached to the finger engaging member 114 and a second latching member 150 is removably attached to the finger engaging member 116.

Figure 12:
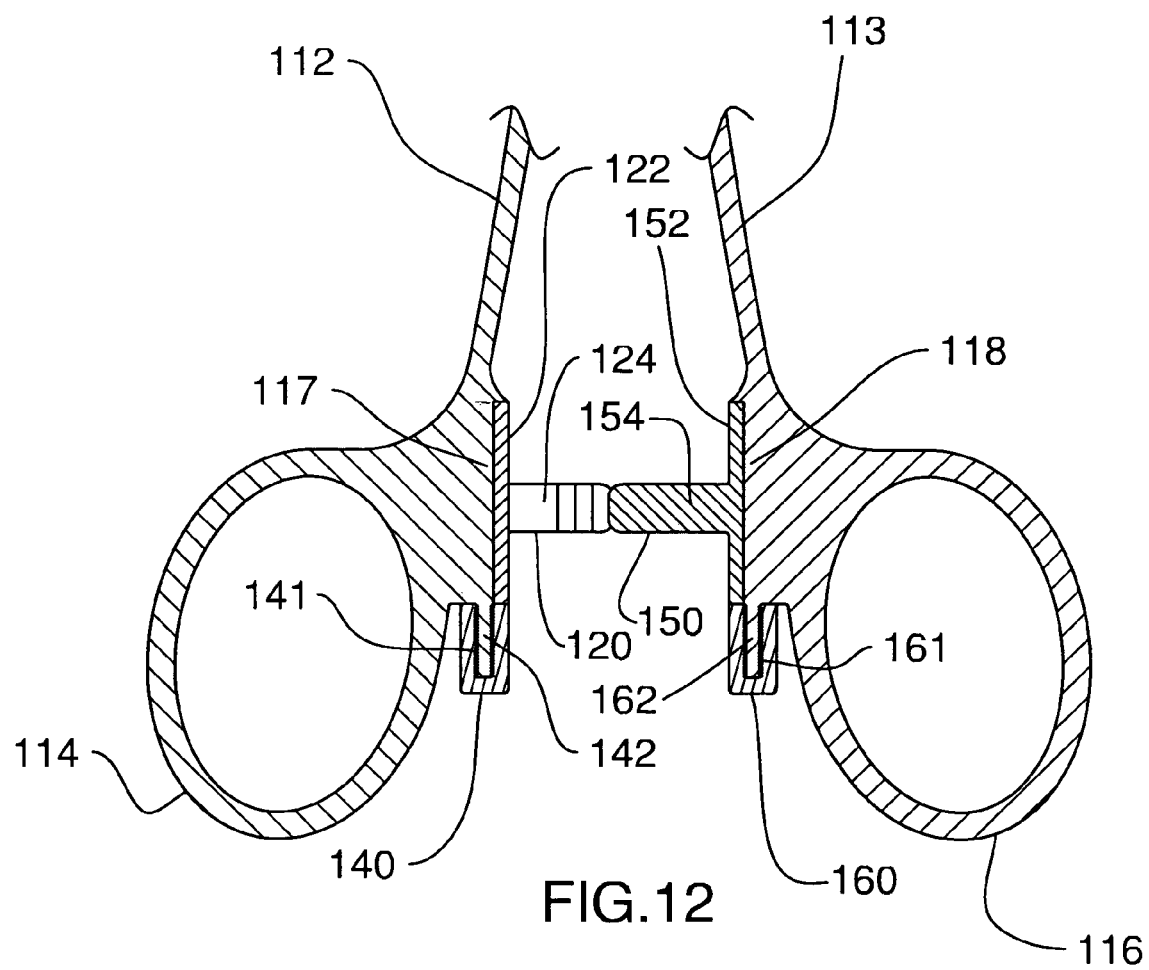
FIG. 12 is an enlarged cross-sectional view of the third alternate embodiment of the present invention.
Figure 14:
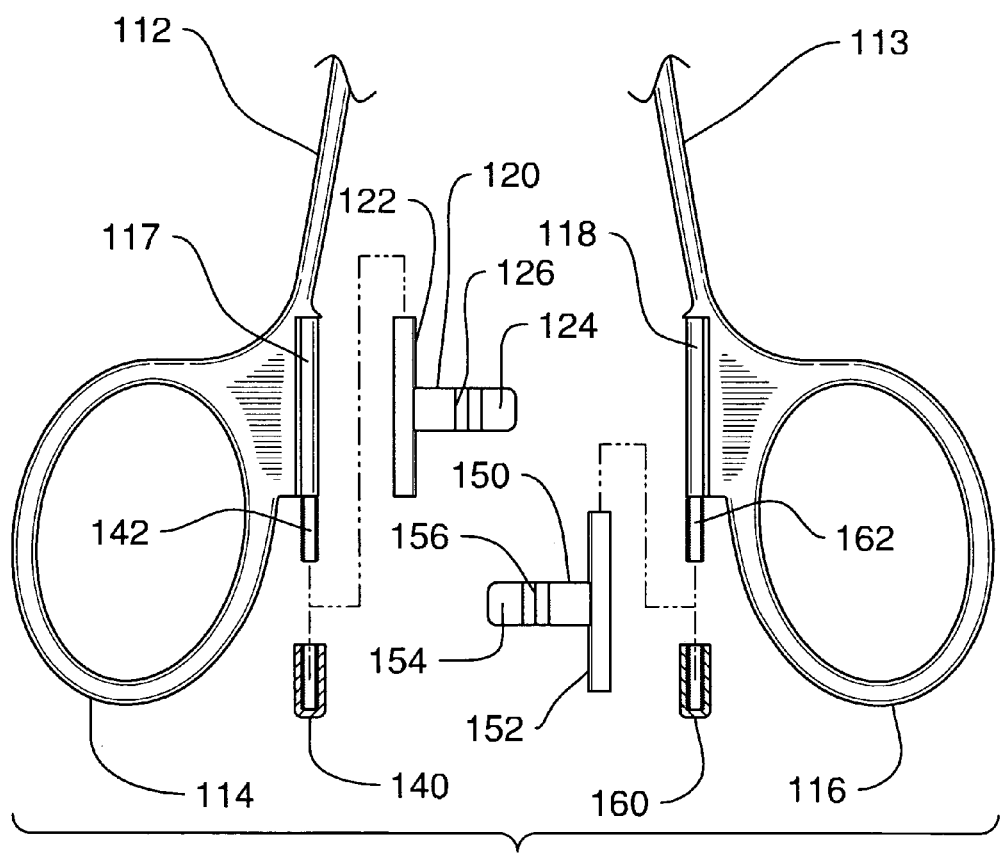
FIG. 14 is an exploded front elevational view of the third alternate embodiment of the present invention.

The retaining caps 140 and 160 have an internal threaded bore 141 and 161. The caps 140 and 160 are adapted to secure the first and second latching members 120 and 150 to the finger engaging members 114 and 116. The caps 140 and 160 are removably attached to the finger engaging members 114 and 116 by screwing the caps onto a threaded stud 142 and 162 which extends out from a protrusion 117 and 118 of the finger engaging members, and adjacent the first and second latching members 120 and 150. This is best illustrated in FIGS. 12 and 14. The caps 140 and 160 may have a smooth or textured surface, or a fastener driving configuration, such as a screw driver or allen wrench head.

The protrusions 117 and 118 extend out from the finger engaging members 114 and 116, and are adapted to slidably receive the first and second latching members 120 and 150. The threaded studs 142 and 162 extend out from the distal ends of protrusions 117 and 118.

The first and second latching members 120 and 150 each have an elongated base 122 and 152 and a latch arm 124 and 154 extending out from each elongated base. The latch arms 124 and 154 feature a plurality of teeth 126 and 156, which are adapted to join and lock together when engaged. The teeth 126 and 156 are able to disengage when pulled apart by the flexing of the first and second elongated members 112 and 113 when an opposing force is applied to the finger, engaging members 114 and 116.

Figure 13:
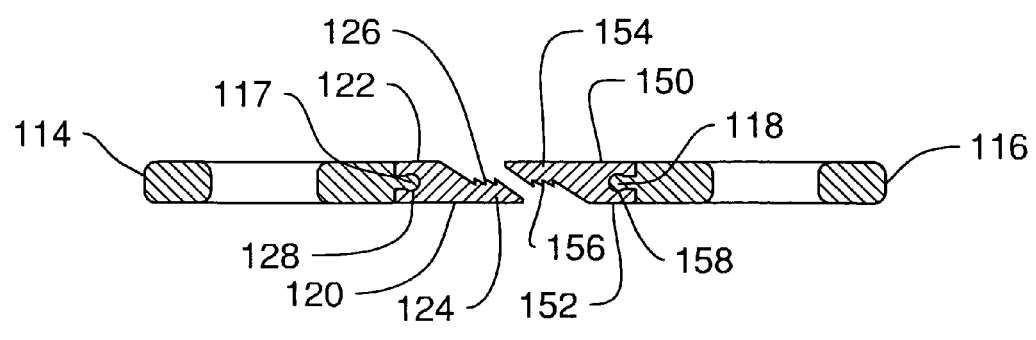
FIG. 13 is a cross-sectional view of the locking assembly of the third alternate embodiment of the present invention.

The elongated base 122 and 152 of the first and second latching members 120 and 150 each have a channel 128 and 158 running the length of the elongated base. The channels 128 and 158 are adapted to slide on and be retained by the protrusions 117 and 118 extending out from the finger engaging members 114 and 116 and adjacent to the threaded studs 142 and 162. The configuration of the channels 128 and 158 and the protrusions 117 and 118 allow the first and second latching members 120 and 150 to slide over the protrusions, but at the same time not allowing the latching members to be pulled off the protrusions in a direction perpendicular to the sliding motion. FIG. 13 best illustrate one possible channel and protrusion configuration.

The first and second latching members 120 and 150 are symmetrical so that they may be removed, inverted and then replaced, thereby changing the orientation of the latching members and allowing a right or left handed user to operate the device 110. Furthermore, other configurations of the first and second latching members 120 and 150 may be used in place of the above described latching members.

Figure 15:
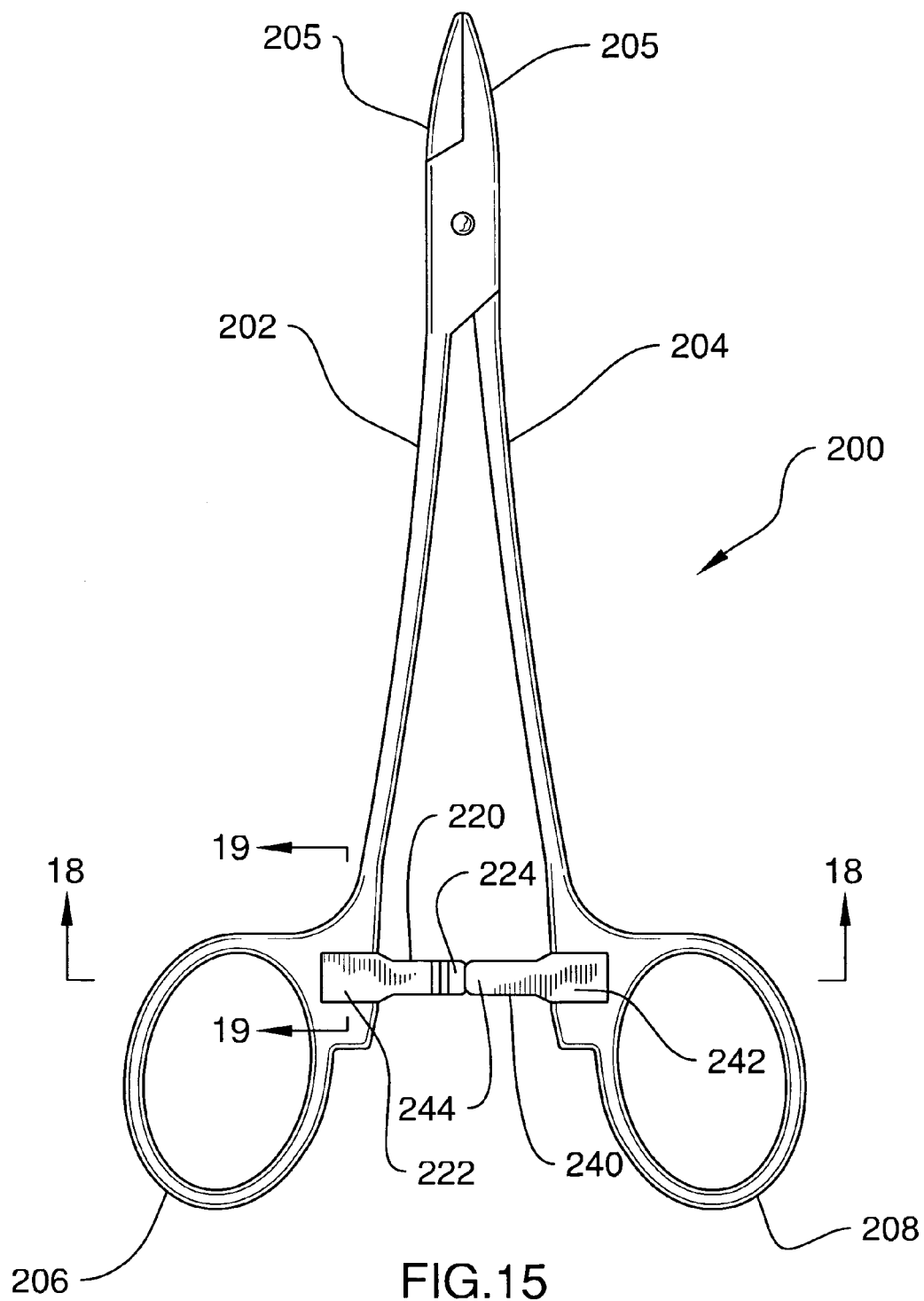
FIG. 15 is a front elevational view of a fourth alternate embodiment of the ambidextrous locking clamp system of the present invention.

Referring now to FIG. 15, a fourth alternate embodiment of the ambidextrous locking clamp system of the present invention is shown and generally designated by the reference numeral 200. More particularly, the ambidextrous locking clamp system 200 has a first elongated member 202 and a second elongated member 204 each having a working head 205, wherein the working heads can be, but not limited to, a gripping jaw or a cutting edge. The second elongated member 204 is connected to the first elongate member 202 via a hinge. The first and second elongated members 202 and 204 each have a finger engaging member 206 and 208 located opposite of the working heads 205. Additionally, a first latching member 220 is removably attached to the finger engaging member 206 and a second latching member 240 is removably attached to the finger engaging member 208.

Figure 16:
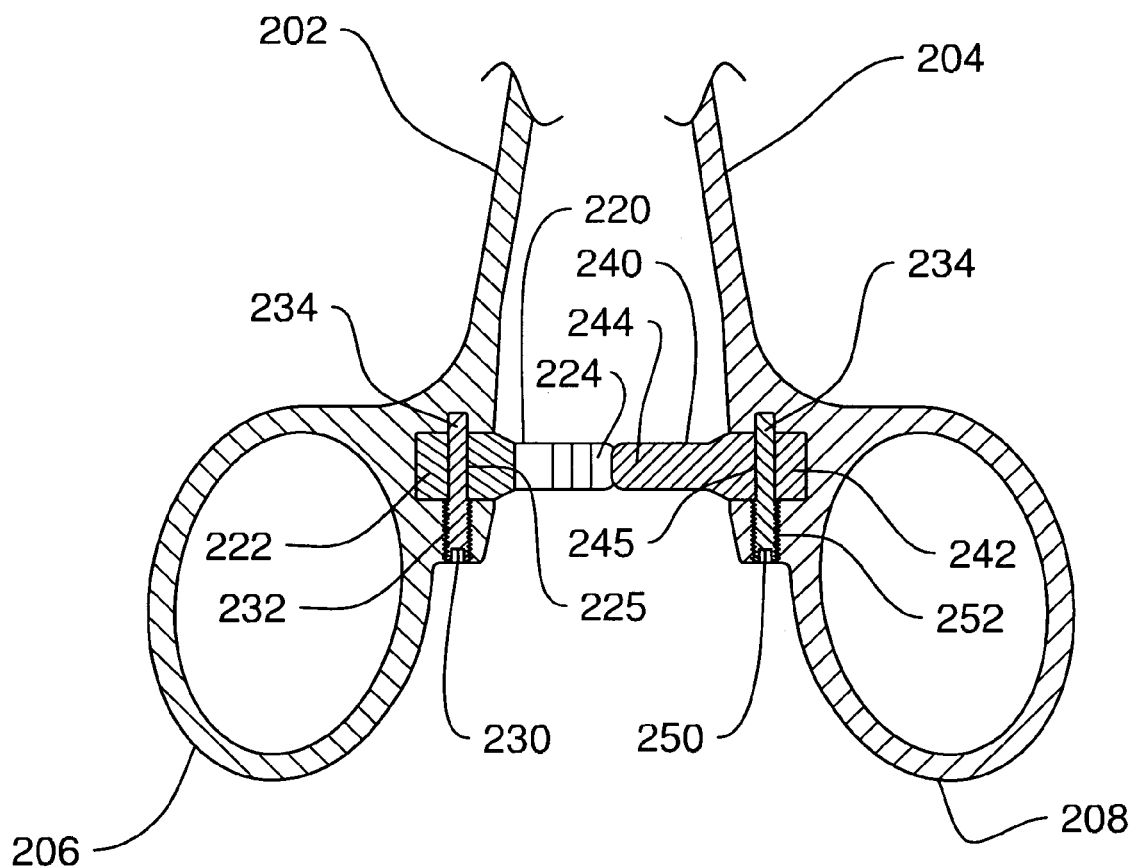
FIG. 16 is an enlarged cross-sectional view of the fourth alternate embodiment of the present invention.

As illustrated in FIG. 16, the first and second latching members 220 and 240 are illustrated in their assembled configuration. The first and second latching members 220 and 240 each have a base 222 and 242 and a latch arm 224 and 244 extending out from each base. The bases 222 and 242 each have an aperture 225 and 245 defined therethrough. A pair of threaded retaining pins 230 and 250 are inserted through a pair of threaded apertures 232 and 252 of the finger engaging members 206 and 208, and through the apertures 225 and 245 of the bases 222 and 242 of the latching members 220 and 240.

Figure 17:
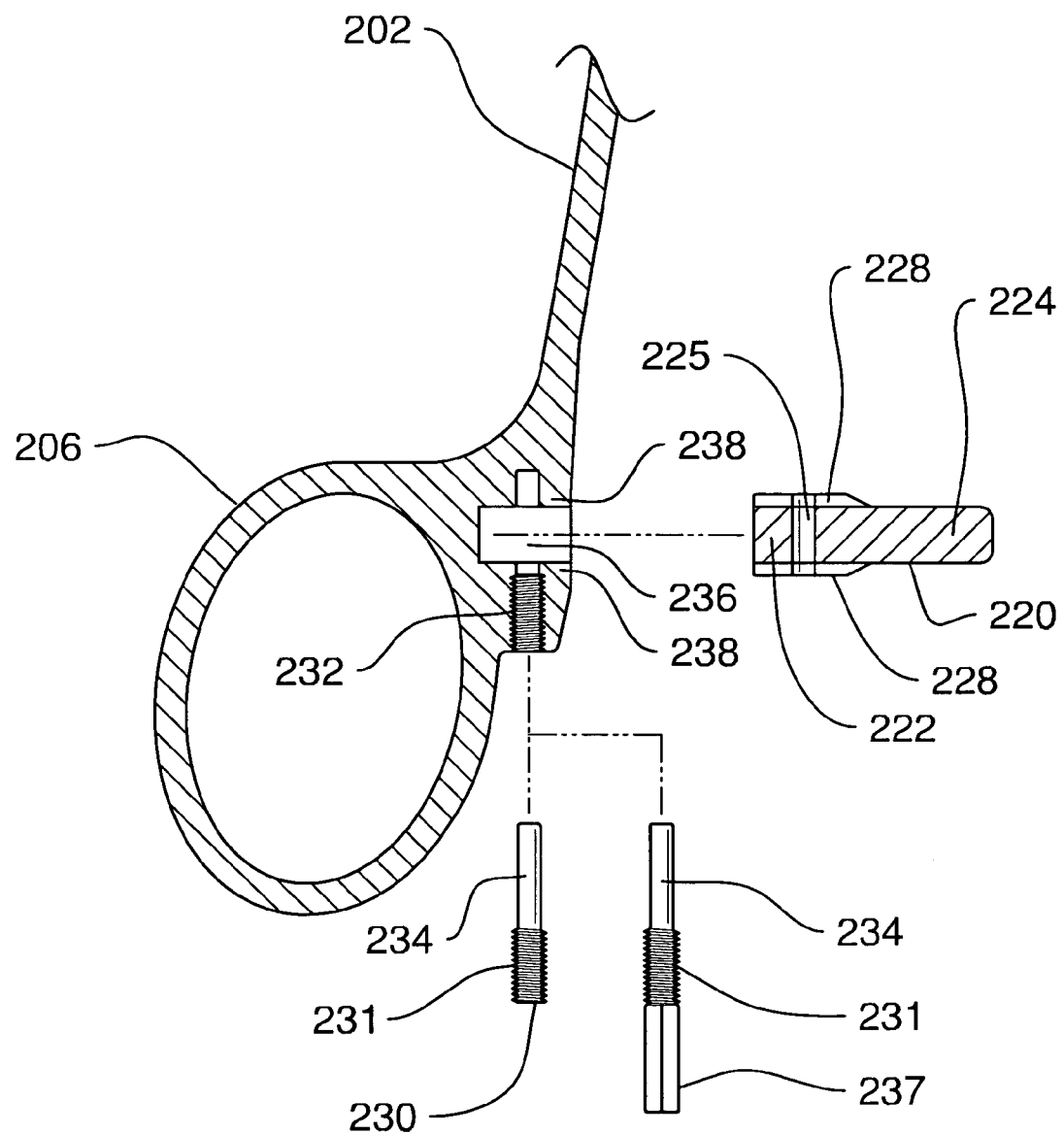
FIG. 17 is an exploded cross-sectional view of the fourth alternate embodiment of the present invention.
Figure 18:
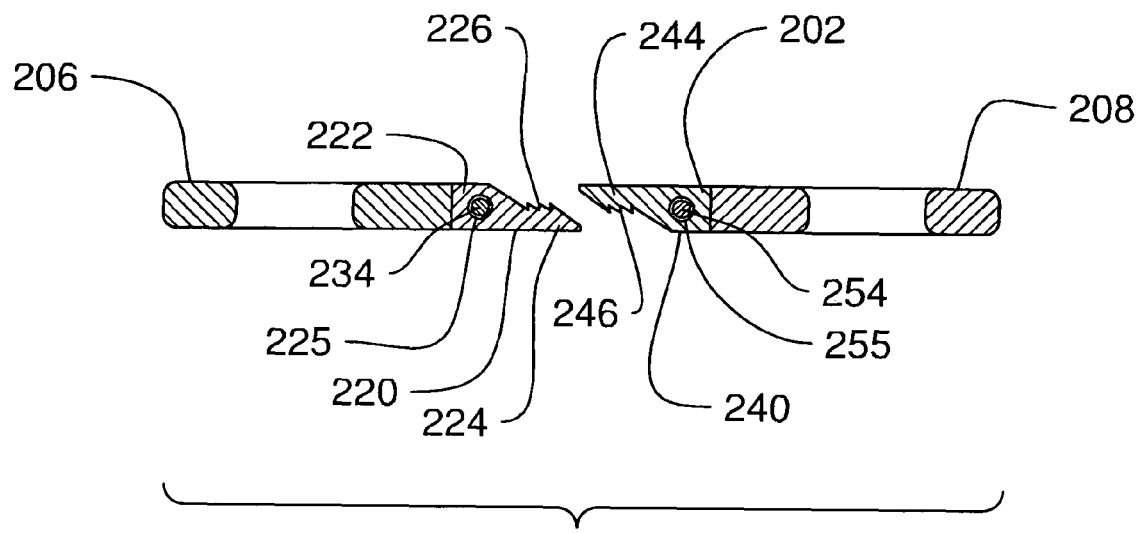
FIG. 18 is a cross-sectional view of the locking assembly of the fourth alternate embodiment of the present invention.
Figure 19:
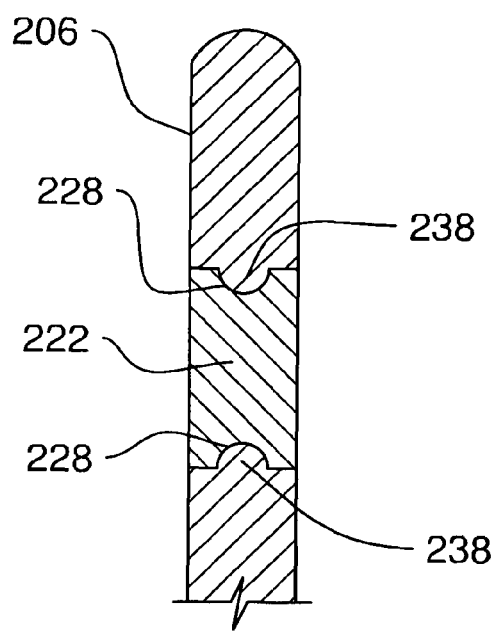
FIG. 19 is a cross-sectional view of the locking assembly of the fourth alternate embodiment of the present invention.

A more detailed illustration of the first latch member 220 and finger engaging member 206 assembly is shown in FIG. 17, whereby the second latch member 240 and finger engaging member 208 assembly is a mirror image thereof and therefor not shown. The threaded retaining pins 230 and 234 have a threaded end 231 featuring a driving head or detent, and a non-threaded section 234. The non-threaded section 234 is adapted to be received through a threaded aperture 232 and 252 of the finger engaging members 206 and 208, and through the apertures 225 and 245 of the latching members 220 and 240. The threaded end 231 engages the threaded apertures 232 and 252 to secure the retaining pins 230 and 250 in the finger engaging members 206 and 208, thereby securing the latching members 220 and 240 in a notch 236 located in each of the finger engaging members. The latching members 220 and 240 are slidably inserted into notches 236 so that the bases 222 and 242 rest in the notches. The bases 222 and 242 of the latching members 220 and 240 have a pair of channels 228 running the length of the base parallel with the longitudinal axis of the latch arms 224 and 244. As best illustrated in FIGS. 17 and 18, the channels 228 are adapted to receive a set of protrusions 238 which extend into the notch 236. The channel 228 and protrusion 238 connection is configured to retain the latching members 220 and 240 in the notch 236 and flush with the outer surface of the finger engaging members 206 and 208. Additionally, the channel 228 and protrusion 238 connection prevents the latching members 220 and 240 from rotating out of alignment with the notch 236. FIG. 18 best illustrate one possible channel and protrusion configuration.

The latch arms 224 and 244 feature a plurality of teeth 226 and 246, which are adapted to join and lock together when engaged. The teeth 226 and 246 are able to disengage when pulled apart by the flexing of the first and second elongated members 202 and 204 when an opposing force is applied to the finger engaging members 206 and 208. The first and second latching members 220 and 240 are symmetrical so that they may be removed, inverted and then replaced, thereby changing the orientation of the latching members and allowing a right or left handed user to operate the device 200. Furthermore, other configurations of the first and second latching members 220 and 240 may be used in place of the above described latching members.

Figure 20:
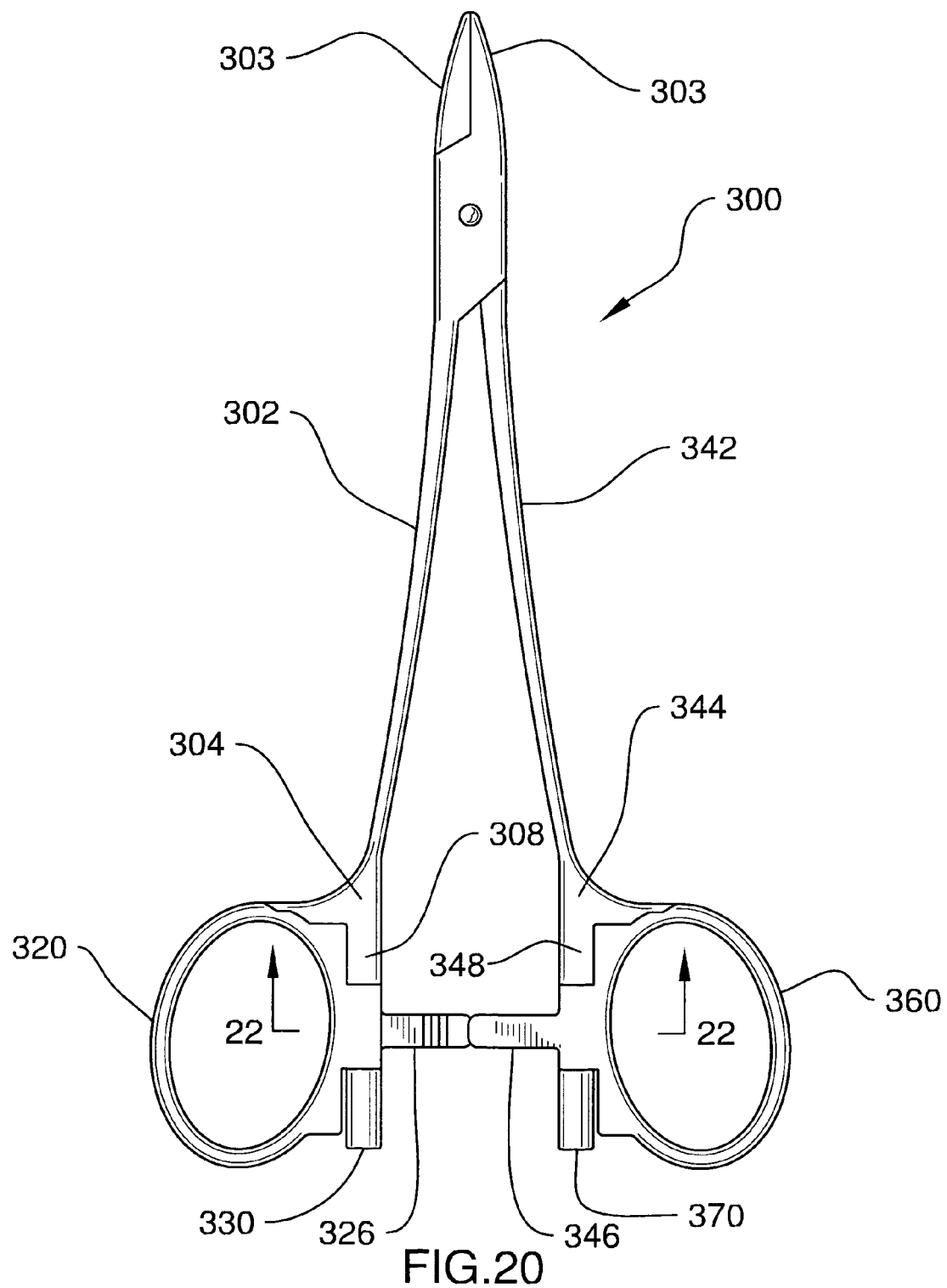
FIG. 20 is a front elevational view of a fifth alternate embodiment of the ambidextrous locking clamp system of the present invention.
Figure 21:
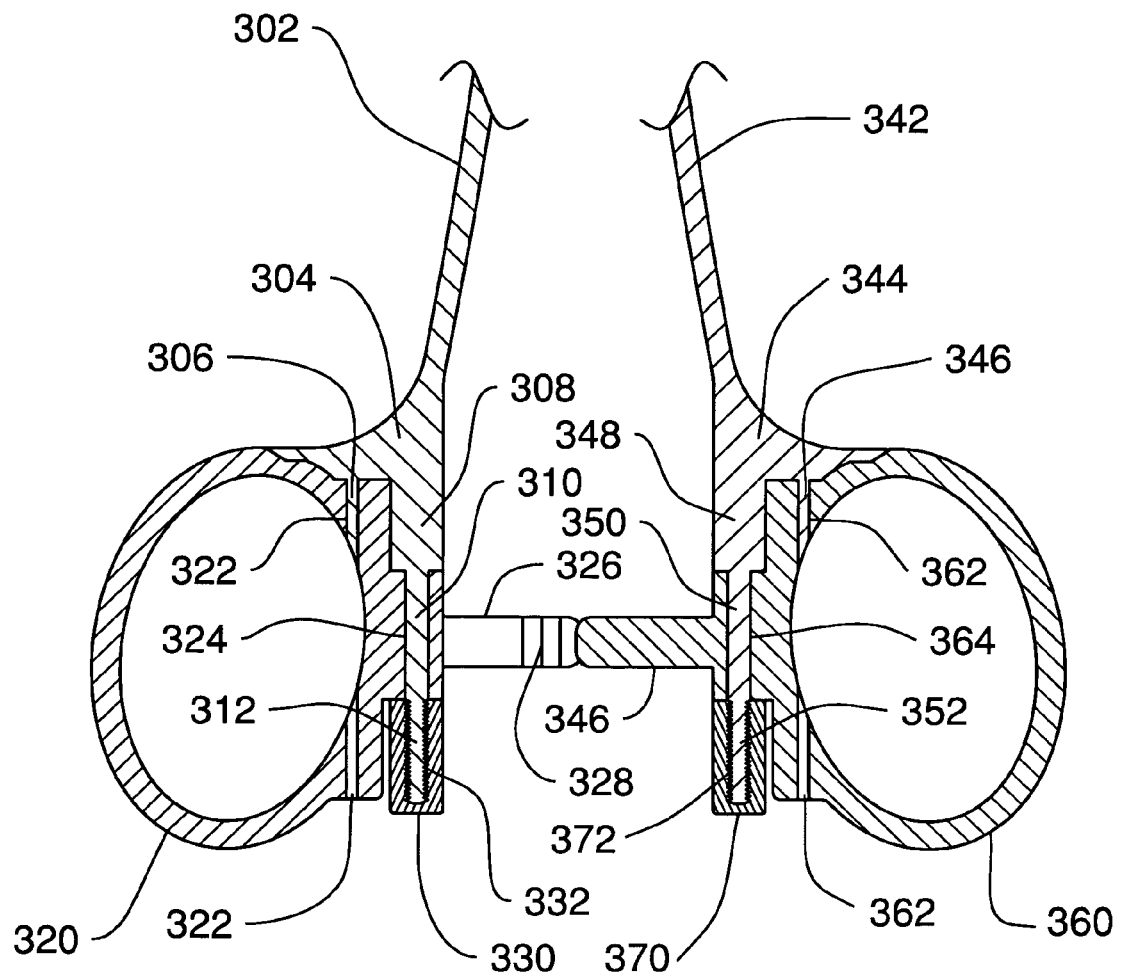
FIG. 21 is an enlarged cross-sectional view of the fifth alternate embodiment of the present invention.
Figure 22:
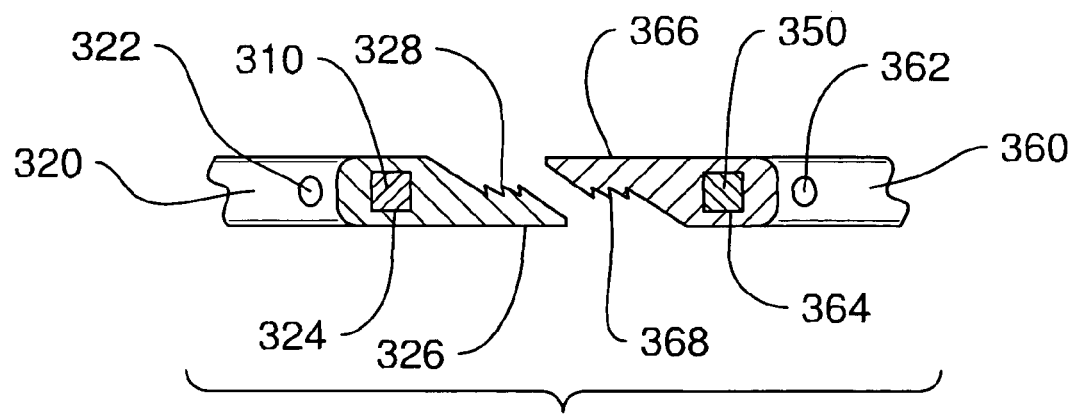
FIG. 22 is a cross-sectional view of the locking assembly of the fifth alternate embodiment of the ambidextrous locking clamp system of the present invention.

Referring now to FIG. 20, a fifth alternate embodiment of the ambidextrous locking clamp system of the present invention is shown and generally designated by the reference numeral 300. More particularly, the ambidextrous locking clamp system 300 has a first elongated member 302 and a second elongated member 342 each having a working head 303, wherein the working heads can be, but not limited to, a gripping jaw or a cutting edge. The second elongated member 342 is connected to the first elongate member 302 via a hinge. The first and second elongated members 302 and 342 each have a removable finger engaging member 320 and 360 located opposite of the working heads 303. Each removable finger engaging member 320 and 360 has a latching arm 326 and 346 extending out and towards each other. A first retaining cap 330 and second retaining cap 370 are threadably attached to the first and second elongated members 302 and 342, and are orientated so that the centerline of the caps are aligned with the longitudinal axis of the first and second elongated members. The retaining caps 330 and 370 can also be orientated in any alternate position to the first and second elongated members 302 and 342. The first and second retaining caps 330 and 370 are adapted to secure the finger engaging members 320 and 360 to the first and second elongated members 302 and 342.

The first and second elongated members 302 and 342 each have a finger engaging member receiving assembly 304 and 344. The finger engaging member receiving assemblies 304 and 344 each have a protrusion 306 and 346, and a retaining rod 308 and 348. The retaining rods 308 and 348 include a stem 310 and 350 extending out therefrom, each with a threaded end 312 and 352. The first and second retaining caps 330 and 370 have internally threaded bores 332 and 372 able to be threaded on to the treaded ends 312 and 352 of the stems 310 and 350.

Figure 23:
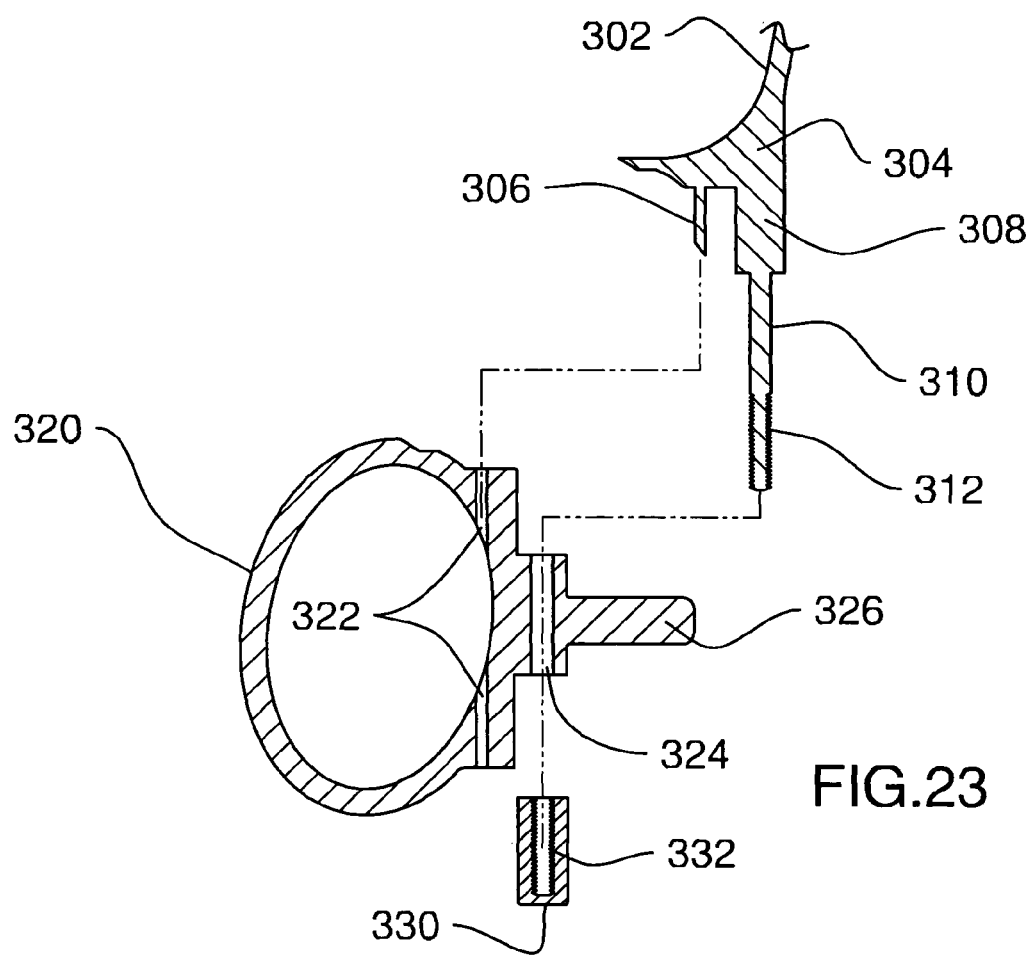
FIG. 23 is an exploded cross-sectional view of the fifth alternate embodiment of the present invention.

The finger engaging members 320 and 360 each have a bore 322 and 362 adapted to receive the protrusions 306 and 346 of the finger engaging, member receiving assemblies 304 and 344. The finger engaging members 320 and 360 also have an aperture 324 and 364 running parallel with the bores 322 and 344, which correspond to the configuration of the stems 310 and 350, and to the retaining rods 308 and 348. The finger engaging members 320 and 360 are positioned on to the protrusions 306 and 346, and to the retaining rods 308 and 348, and are then secured to the finger engaging member receiving assemblies 304 and 344 by securing the retaining caps 330 and 370 on to the threaded ends 312 and 352 of stems 310 and 350, as best illustrated in FIG. 23.

The latching arms 326 and 366 each have a plurality of teeth 328 and 368, which are adapted to join and lock together when engaged. The teeth 328 and 368 are able to disengage when pulled apart by the flexing of the first and second elongated members 302 and 342 when an opposing force is applied to the finger engaging members 320 and 360. The first and second finger engaging members 320 and 360 are symmetrical so that they may be removed, inverted and then replaced, thereby changing the orientation of the latching members and allowing a right or left handed user to operate the device 300. Furthermore, other configurations of the first and second finger engaging members 320 and 360 may be used in place of the above described latching members.

In use, it can now be understood that either a right hand or left hand user can use the ambidextrous locking clamp system. The user would remove and reverse the orientation of the removable latching member or the removable finger engaging member which features a latching arm. By doing this, the user can change the operational configuration of the ambidextrous locking device. The ambidextrous locking clamp system can use a variety of retaining means, such as, but not limited to, a rotating lever, a threaded cap, or a retaining pin. All of these retaining means can be used to secure the removable latching member or the removable finger engaging member from the elongated members.

While a preferred embodiment of the ambidextrous locking clamp system has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. For example, any suitable sturdy material may be used for the manufacture of the ambidextrous locking clamp system. And although manipulating objects with a tool having removable latching members have been described, it should be appreciated that the ambidextrous locking clamp system herein described is also suitable for all types of hand operated locking tools having a at least two hingedly connected arms.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An ambidextrous locking clamp system for providing a user the ability to alter the configuration of a hand operated device allowing a right hand or left hand user to operate the device comprising:

a first elongated member having a finger engaging member, at least one protrusion extending from said finger engaging member, and a working head;

a second elongated member having a finger engaging member, at least one protrusion extending from said finger engaging member of said second elongated member, and a working head, said second elongated member being hingedly connected to said first elongated member so said protrusions of said first and second elongated members substantially face each other;

at least two latching members each having a base, and a latching arm extending from said base, said latching arms being adapted to removably engage each other;

a first lever rotatably attached to said finger engaging member of said first elongated member, said first lever having an extended portion for operation by a user, said first lever retains said latching member on said protrusion of said first elongated member and allows said latching member to be removed from said first elongated member when said first lever is rotated; and a second lever rotatably attached to said finger engaging member of said second elongated member, said first lever having an extended portion for operation by a user, said second lever retains said latching member on said protrusion of said second elongated member and allows said latching member to be removed from said second elongated member when said second lever is rotated;

wherein each of said latching members having at least one channel defined along said base parallel with a longitudinal axis of said base, said channel having a shape corresponding with said protrusions of said first and second elongated members and being adapted to receive said protrusion of said first and second elongated members respectively;

wherein said latching members are slidably attached to said first and second elongated members in a direction parallel with the longitudinal axis of said base of said latching members.

2. The ambidextrous locking clamp system of claim 1, wherein said finger engaging members of said first and second elongated members each further comprising a pivot pin extending out therefrom and through said first and second levers respectively allowing said first and second levers to rotate.

3. The ambidextrous locking clamp system of claim 2, wherein said first lever further comprising an extension for retaining said first or second latching member respectively on said protrusion of said finger engaging member of said first elongated member when aligned with a longitudinal axis of said protrusion of said first elongated member, and wherein said second lever further comprising an extension for retaining said first or second latching member respectively on said protrusion of said finger engaging member of said second elongated member when aligned with a longitudinal axis of said protrusion of said second elongated member.

4. The ambidextrous locking clamp system of claim 3, wherein each of said extended portions of said first and second levers being contoured to conform to a shape of a portion of said finger engaging member adjacent thereto.

5. The ambidextrous locking clamp system of claim 4, wherein said protrusions of said finger engaging members each being configured to slidably receive at least one of said latching members, while not allowing said latching members to be removed in a direction other than the direction of insertion.

6. The ambidextrous locking clamp system of claim 5, wherein said first and second levers each further comprising a notch defined therein and adapted to allow said first and second latching members respectively to pass therethrough when rotated.

7. The ambidextrous locking clamp system of claim 1, wherein said latching members each having a plurality of teeth adapted to engage each other when said latching members are joined.

8. The ambidextrous locking clamp system of claim 1, wherein said latching members are adapted to be interchangeably and reversibly attachable to said protrusions of said first and second elongated members respectively.

9. An ambidextrous locking clamp system comprising:
a first elongated member having a finger engaging member, at least one protrusion extending from said finger engaging member, and a working head opposite of said finger engaging member;
a second elongated member having a finger engaging member, at least one protrusion extending from said finger engaging member, and a working head opposite of said finger engaging member, said second elongated member being hingedly connected to said first elongated member so said protrusions of said first and second elongated members substantially face each other;
at least two latching members each having a base, a latching arm extending from said base, and a channel defined along said base parallel with a longitudinal axis of said base, said channels having a shape corresponding with said protrusions of said first and second elongated members and being adapted to slidably receive said protrusions of said first and second elongated members respectively, said latching arms of said latching members each having a plurality of teeth adapted to engaged each other;

a first lever rotatably attached to said finger engaging member of said first elongated member adjacent said protrusion thereof, said first lever being adapted to retain said latching member received on said protrusion thereof and allow said latching member to be removed from said first elongated member when said first lever is rotated; and
a second lever rotatably attached to said finger engaging member of said second elongated member adjacent said protrusion thereof, said second lever being adapted to retain said latching member received on said protrusion thereof and allow said latching member to be removed from said second elongated member when said second lever is rotated.

10. The ambidextrous locking clamp system of claim 9, wherein said finger engaging members of said first and second elongated members each further comprising a pivot pin extending out therefrom and through said first and second levers respectively allowing said first and second levers to rotate.

11. The ambidextrous locking clamp system of claim 10, wherein said first lever further comprising an extension for retaining said first or second latching member respectively on said protrusion of said finger engaging member of said first elongated member when aligned with a longitudinal axis of said protrusion of said first elongated member, and wherein said second lever further comprising an extension for retaining said first or second latching member respectively on said protrusion of said finger engaging member of said second elongated member when aligned with a longitudinal axis of said protrusion of said second elongated member.

12. The ambidextrous locking clamp system of claim 11, wherein said first and second levers each further comprising an extended portion for easy operation by a user, each of said extended portions being contoured to conform to a shape of a portion of said finger engaging member adjacent thereto.

13. The ambidextrous locking clamp system of claim 12, wherein said protrusions of said first and second elongated members each being configured to slidably receive at least one of said latching members, while not allowing said latching members to be removed in a direction other than the direction of insertion.

14. An ambidextrous locking clamp system comprising:
a first elongated member having a finger engaging member, a working head opposite of said finger engaging member, a pivot pin extending out from said finger engaging member, and a protrusion extending out from said finger engaging member of said first elongated member;
a second elongated member having a finger engaging member, a working head opposite of said finger engaging member, a pivot pin extending out from said finger engaging member of said second elongated member, and a protrusion extending out from said finger engaging member of said second elongated member, said second elongated member being hingedly connected to said first elongated member so said protrusions of said first and second elongated members substantially face each other;
at least two latching members each having a base, a channel defined along said base, and a latching arm extend from said base, said latching arm having a plurality of teeth, said channels having a shape corresponding with said protrusions of said first and second elongated members and adapted to slidably receive said protrusions of said first and second elongated members, wherein one of said latching members being slidably received on said protrusion of said first elongated member, and the other of said latching members being slidably received on said protrusion of said second elongated member so that said teeth of said latching members being engagable with each other, said channels being defined along said bases parallel with a longitudinal axis of said base;

a first lever rotatably attached to said pivot pin of said first elongated member adjacent said protrusion thereof, said first lever being adapted to retain said latching member received on said protrusion thereof and allow said latching member to be removed from said first elongated member when said first lever is rotated; and a second lever rotatably attached to said pivot pin of said second elongated member adjacent said protrusion thereof, said second lever being adapted to retain said latching member received on said protrusion thereof and allow said latching member to be removed from said second elongated member when said second lever is rotated.

15. The ambidextrous locking clamp system of claim 14, wherein said protrusions of said first and second elongated members each being configured to slidably receive at least one of said latching members, while not allowing said latching members to be removed in a direction other than the direction of insertion.

* * * * *